US005755362A

United States Patent [19]
Rodriguez, Jr. et al.

[11] Patent Number: 5,755,362
[45] Date of Patent: May 26, 1998

[54] HAND-HELD APPLICATOR WITH FORCE LIMITING CLUTCH

[75] Inventors: Alex Rodriguez, Jr., Woodbury; James E. Nash, St. Paul; Thomas W. Martin, Maplewood, all of Minn.

[73] Assignee: Minnesota Mining & Manufacturing Co., St. Paul, Minn.

[21] Appl. No.: 547,370

[22] Filed: Oct. 24, 1995

Related U.S. Application Data

[63] Continuation-in-part of Ser. No. 394,711, Feb. 27, 1995, abandoned.

[51] Int. Cl.$^6$ .......................................................... B67D 5/42
[52] U.S. Cl. .............................................. 222/391; 433/90
[58] Field of Search .................................. 222/327, 391; 604/209, 210, 224; 433/90

[56] References Cited

U.S. PATENT DOCUMENTS

| | | | |
|---|---|---|---|
| 1,536,477 | 5/1925 | Crewe | 222/391 |
| 2,229,839 | 1/1941 | Crewe | 74/169 |
| 2,889,085 | 6/1959 | Collins | 222/391 |
| 2,933,221 | 4/1960 | Rand et al. | 222/391 |
| 3,069,053 | 12/1962 | Nilsson | 222/391 |
| 3,311,265 | 3/1967 | Creighton, Jr. et al. | 222/391 X |
| 3,517,668 | 6/1970 | Brickson | 128/218 |
| 3,894,663 | 7/1975 | Carhart et al. | 222/309 |
| 4,198,756 | 4/1980 | Dragan | 222/326 |
| 4,366,919 | 1/1983 | Anderson | 222/137 |
| 4,431,414 | 2/1984 | Lawrence | 433/90 |
| 4,444,560 | 4/1984 | Jacklich | 604/224 |
| 4,472,141 | 9/1984 | Dragan | 433/90 |
| 4,479,781 | 10/1984 | Herold et al. | 433/90 |
| 4,509,662 | 4/1985 | Weiss | 222/391 |
| 4,526,303 | 7/1985 | Harrod | 222/386.5 |
| 4,538,920 | 9/1985 | Drake | 222/145 X |
| 4,708,650 | 11/1987 | Holewinski et al. | 433/90 |
| 4,801,008 | 1/1989 | Rich | 206/219 |
| 4,820,287 | 4/1989 | Leonard | 604/209 |
| 4,913,553 | 4/1990 | Falco | 366/129 |
| 4,993,948 | 2/1991 | Cameron et al. | 433/90 |
| 4,995,540 | 2/1991 | Colin et al. | 222/132 |
| 5,005,735 | 4/1991 | Keller | 222/137 |
| 5,022,563 | 6/1991 | Marchitto et al. | 222/327 |
| 5,052,927 | 10/1991 | Discko, Jr. | 433/90 |
| 5,064,098 | 11/1991 | Hutter, III et al. | 222/137 |
| 5,080,493 | 1/1992 | McKown et al. | 366/177 |
| 5,100,320 | 3/1992 | Martin et al. | 433/90 |
| 5,125,836 | 6/1992 | Dragan et al. | 433/90 |
| 5,129,825 | 7/1992 | Discko, Jr. | 433/90 |
| 5,137,181 | 8/1992 | Keller | 222/134 |
| 5,165,890 | 11/1992 | Discko, Jr. | 433/90 |
| 5,236,108 | 8/1993 | House | 222/232 |
| 5,248,068 | 9/1993 | Goergen et al. | 222/326 |
| 5,306,147 | 4/1994 | Dragan et al. | 433/90 |
| 5,330,079 | 7/1994 | Keller | 222/135 |
| 5,336,014 | 8/1994 | Keller | 403/24 |
| 5,386,931 | 2/1995 | Jacobsen et al. | 222/237 |
| 5,624,260 | 4/1997 | Wilcox et al. | 433/90 |

FOREIGN PATENT DOCUMENTS

62-43634 of 0000 Japan.

*Primary Examiner*—Kenneth Bomberg
*Attorney, Agent, or Firm*—James D. Christoff

[57] ABSTRACT

An applicator has a ratchet mechanism for dispensing material from a single or multiple barrel container. The ratchet mechanism includes a clutch that substantially prevents movement of a plunger of the applicator whenever a resistance to plunger movement is greater than a certain value. As a consequence, bursting of the container, or damage to components of the applicator, is substantially avoided. A resilient, integral pawl hinders unintentional rearward movement of the plunger and provides for a compact construction especially suitable for use in dispensing dental material.

17 Claims, 8 Drawing Sheets

HAND-HELD APPLICATOR WITH FORCE LIMITING CLUTCH

This application is a continuation-in-part of U.S. Ser. No. 08/394,711 filed Feb. 27, 1995, now abandoned.

BACKGROUND OF THE INVENTION

1. Field of the Invention

This invention broadly relates to a hand-held applicator having a ratchet drive mechanism for dispensing material from one or more containers, such as a caulking gun, a single- or multiple-barrel syringe, a collapsible tube applicator or other type of dispenser.

2. Description of the Related Art

A wide variety of hand-held applicators are available for dispensing material from one or more containers. Caulking guns, for example, are often used to dispense not only caulk but also adhesives, sealants and other materials as desired. Examples of caulking guns are described in U.S. Pat. Nos. 4,509,662 and 5,386,931.

Hand-held applicators are also widely used in the field of medicine, and particularly in the field of dentistry, for dispensing material to a certain location when desired. Examples of applicators for dispensing dental material from a single-barrel container are described in U.S. Pat. Nos. 4,444,560, 4,708,650 and 5,125,836.

Some applicators have more than one barrel, and often include linked together plungers that dispense equal portions of material from each barrel simultaneously. An example of an applicator that is also known as a double-barrel dispensing syringe is described in U.S. Pat. No. 4,538,920 which is assigned to the assignee of the present invention. The syringe described in U.S. Pat. No. 4,538,920 includes an exit conduit having a plurality of helical static mixing elements so that materials dispensed from the barrels are thoroughly mixed during passage through the exit conduit and mixing by hand can be avoided.

Double-barrel dispensing syringes having static mixing elements are widely used in dentistry for storing, mixing and dispensing impression material. Such syringes often hold a catalyst component in one chamber and a base component in another chamber. The mixed components dispensed from the exit conduit can be placed directly without further mixing into an impression tray or, alternatively, directly into the oral cavity.

Some hand-held applicators are intended to be disposed of once material in the container has been exhausted. Such applicators may include a housing that is integral with a container having a quantity of material to be dispensed. Many other types of applicators, however, are constructed to detachably receive a container and are often called cartridge dispensers. Cartridge dispensers include many types of household and industrial caulking guns that receive single tube-shaped containers of material, as well as single- and multiple-barrel dental dispensers that are adapted to receive single barrel or multiple barrel containers.

Conventional applicators often include a housing having a receptacle for receiving a container of material to be dispensed, a handle connected to the housing and an arm connected to the housing. Typically, the arm is pivotally coupled to the housing and, when moved relative to the housing, advances a plunger toward the container. The forward end of the plunger engages a piston in the container and advancement of the plunger and piston causes material to be dispensed through a front opening of the container.

Some applicators, such as the applicator described in U.S. Pat. No. 5,125,836, are adapted to releasably receive a relatively small container of material to be dispensed, such as a container adapted for a single use. These applicators often include a plunger that connects directly to or bears against a movable arm. Movement of the arm in a single stroke advances the plunger sufficiently to expel substantially all of the contents of the container.

Other applicators are adapted to receive larger containers that are likely to be used during several different occasions before the container is depleted. Such applicators often include a ratchet mechanism wherein the plunger is moved only a relatively small distance as an arm of the applicator is moved through its normal full stroke. Ratchet mechanisms are often utilized on caulking guns and double-barrel syringes and are satisfactory in an ergonomic sense because the ratchet mechanism provides sufficient mechanical advantage in most instances for the user to easily expel the material in the cartridge.

Many hand-held applicators are suitable only for dispensing material having a relatively low viscosity. If, for example, the viscosity of the material exceeds a certain value, the material may be difficult to dispense through the relatively small front opening of the container. Dispensing of relatively viscous material is also more difficult when the applicator includes a static mixing tip having a tortuous flow path for mixing the components before the latter are discharged to an application site.

Moreover, the viscosity of material in the container may significantly increase in some instances before it is dispensed. For example, the material in the container may inadvertently cure or otherwise thicken or harden before there is an opportunity to discharge the material from the container. In such occurrences, the user may apply a considerable amount of force to the arm of the applicator in an attempt to dispense the material from the container. Such efforts may result in bursting of the container, creating a messy situation that may be difficult to clean. Excessive pressure on the applicator arm may also damage the plunger, the advancement mechanism or other components of the applicator to such a degree that the applicator is no longer useful for its intended purpose.

Applicators with ratchet mechanisms occasionally burst the container or damage components of the applicator when material in the container cannot be easily expelled, because the ratchet mechanism provides significant mechanical advantage that can result in the plunger presenting considerable pressure to the container. The mechanical advantage can be so substantial that the user may be unaware of the potential for damage to the container or components of the applicator. The potential for damage is greater when smaller containers or static mixers with smaller internal passages are used, or when an attempt is made to dispense relatively viscous pastes from the container.

Many ratchet mechanisms for hand-held applicators include a first pawl or follower and a second pawl or follower. The first pawl is connected to the movable arm of the applicator and engages a row of rack teeth on the plunger for driving the plunger in a forward direction. When the arm is released, the first pawl pivots to disengage the teeth and move rearwardly for contact with a rearward tooth so that the plunger can be further advanced when the arm is subsequently moved. The second pawl is often provided to prevent rearward movement of the plunger when the arm is released and the first pawl rides across the teeth in a rearward direction. The second pawl is often connected to an outwardly extending tab that, when depressed, pivots the second pawl to allow the user to pull back the plunger from the cartridge once emptied.

In applicators with first and second pawls, the pawls are often connected to respective separate, coil metal springs that serve to bias the pawls into a position of contact with the teeth. Such construction is generally satisfactory for many uses but is somewhat bulky when used in certain applications. In the dental field, for example, there is a continuing need to make the overall size of the applicator as small as practical so that viewing of the dispensing operation is not unduly obstructed.

It is also known that the inner chamber diameter of one type of cartridge for certain double-barrel dispensing applicators slightly increases when pressure in the cartridge is greater than a certain value. If the inner diameter increases beyond a certain amount due to internal pressure in the cartridge, the pistons of the cartridge are unable to engage the inner chamber walls with sufficient frictional force to remain in place as the arm of the applicator is released in an attempt to move the pawl or follower of the ratchet mechanism rearward to engage the next tooth in the plunger. Further, unlike the dispensing applicators mentioned above, this type of applicator lacks a second pawl to prevent rearward movement of the plunger as the arm is released. As such, the plunger moves rearwardly whenever pressure in the cartridge is sufficient to overcome any frictional forces between the cartridge piston and the expanded chamber wall, with the result that the ratchet mechanism toggles and is unable to further advance such that bursting of the cartridge is often avoided. However, such a result is closely dependent upon the tolerances between the cartridge piston and the chamber wall which may vary in production or from manufacturer to manufacturer.

SUMMARY OF THE INVENTION

The present invention in one aspect is directed toward an applicator for dispensing material from a container. The applicator comprises a housing having a receptacle for receiving a container of material to be dispensed, and an elongated plunger coupled to the housing and movable relative to the housing in a longitudinal direction toward the receptacle. A handle is connected to the housing, and an arm is coupled to the housing adjacent the handle and is movable relative to the housing. A follower is coupled to the arm and has a portion engagable with the plunger for driving movement of the plunger in a longitudinal direction toward the receptacle as the arm is moved relative to the housing. The applicator includes a clutch for substantially preventing movement of the plunger toward the receptacle as the arm is moved relative to the housing whenever movement of the plunger is hindered by resistance that is greater than a certain value.

In the various embodiments of the invention, the clutch is useful for reliably preventing damage to the applicator or to the container received in the applicator. For example, if material cannot be discharged from the container because the material has unintentionally thickened or because an outlet of the container has been plugged, the clutch prevents advancement of the plunger past a certain position so that damage to the plunger, the receptacle and other parts of the applicator will normally be avoided. The clutch also prevents the plunger from applying undue pressure to the container or a piston of the container so that the likelihood of rupturing the container is significantly reduced.

Another aspect of the invention is directed toward an applicator for dispensing material from a container, wherein the applicator comprises a housing having a receptacle for receiving a container of material to be dispensed. The applicator includes an elongated plunger coupled to the housing and movable relative to the housing in a forward, longitudinal direction toward the receptacle, and the plunger has a row of rack teeth. A handle is connected to the housing, and an arm is coupled to the housing adjacent the handle and is movable relative to the housing. A follower is coupled to the arm and has a portion engagable with the row of rack teeth for driving movement of the plunger in the forward direction toward the receptacle as the arm is moved relative to the housing. The applicator also includes a pawl for hindering movement of the plunger in a rearward direction away from the receptacle. The pawl has a first section connected to the housing and a second section having a tooth engagable with the row of rack teeth. The first section and the second section are integral and made of a resilient material such that the tooth is yieldably biased toward the row of rack teeth.

Other aspects and advantages of the present invention will become apparent following a review of the drawings and a reading of the detailed description that follow.

DETAILED DESCRIPTION OF THE PREFERRED EMBODIMENTS

An applicator for dispensing material from a container is broadly designated by the numeral 10 in FIGS. 1–5. The applicator 10 includes a housing 12 that has a hollow upper portion and a depending handle 14 that is fixed to the upper portion. The housing 12 is constructed of two joined-together sections that are integrally molded of a synthetic resinous material (such as RADEL brand polyphenylsulfone, no. R5100; from Amoco).

Figure 3:
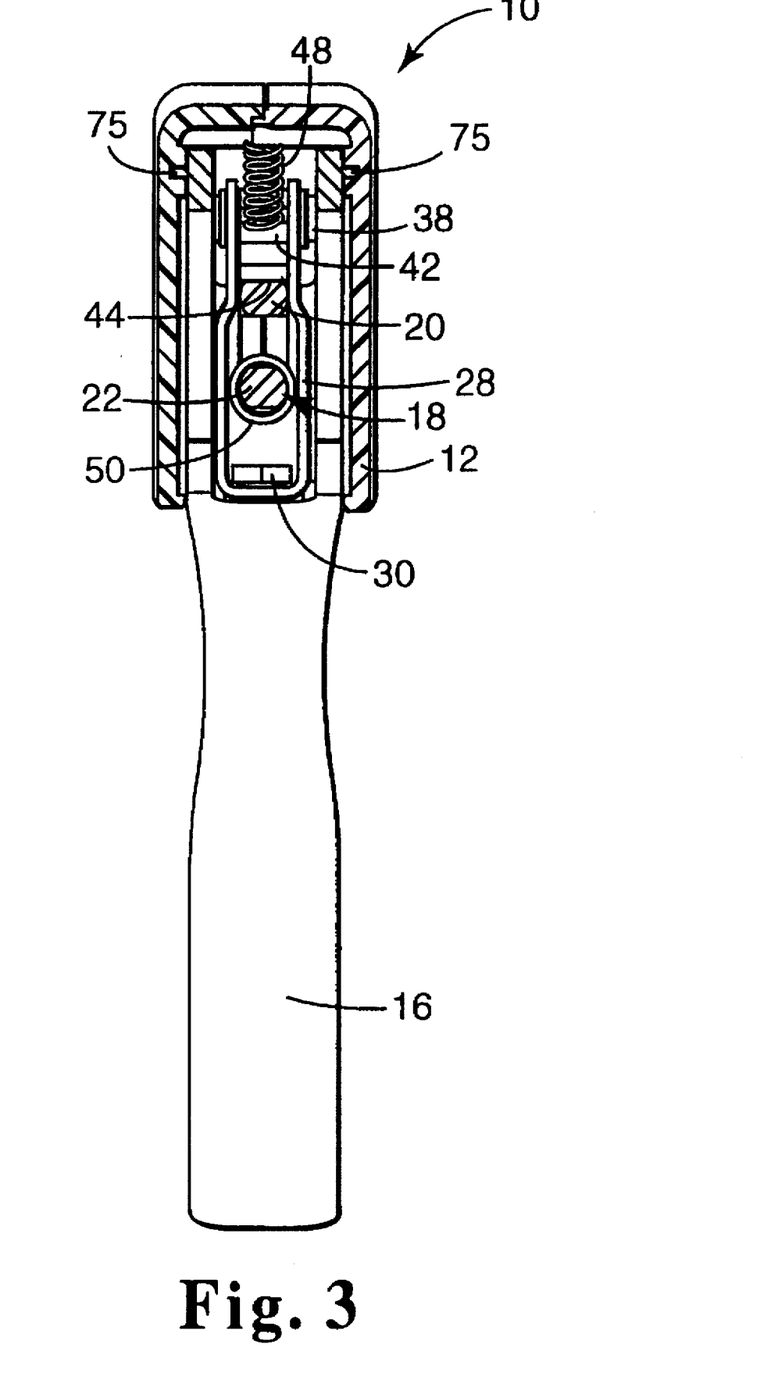
FIG. 3 is an elevational view in partial section of the applicator shown in FIG. 2, taken along lines 3—3 of FIG. 2.

The applicator 10 also includes an arm 16 that depends from the upper portion of the housing 12 and is located next to the handle 14. An upper portion of the arm 16 is bifurcated and straddles opposite sides of a plunger 18. A lower portion of the arm 16 is hollow and presents a recess. As shown in FIG. 3, each side of the upper, bifurcated portion of the arm 16 has an outwardly extending cylindrical boss 75 that is received in a socket of the housing 12 for pivotally coupling the arm 16 to the housing 12.

The plunger 18 includes an upper and lower plunger rod 20, 22 respectively that are integrally connected together by a handle or ring 24. Both of the plunger rods 20, 22 pass through respective pairs of aligned holes formed in the upper portion of the housing 12. Each plunger rod 20, 22 includes an enlarged, forward head for engaging pistons in the container. Each head is larger than the holes in the housing 12 so that the plunger 18 cannot be inadvertently detached from the housing 12. The top of the upper plunger rod 20 also has a row of flat rack teeth 26.

Figure 2:
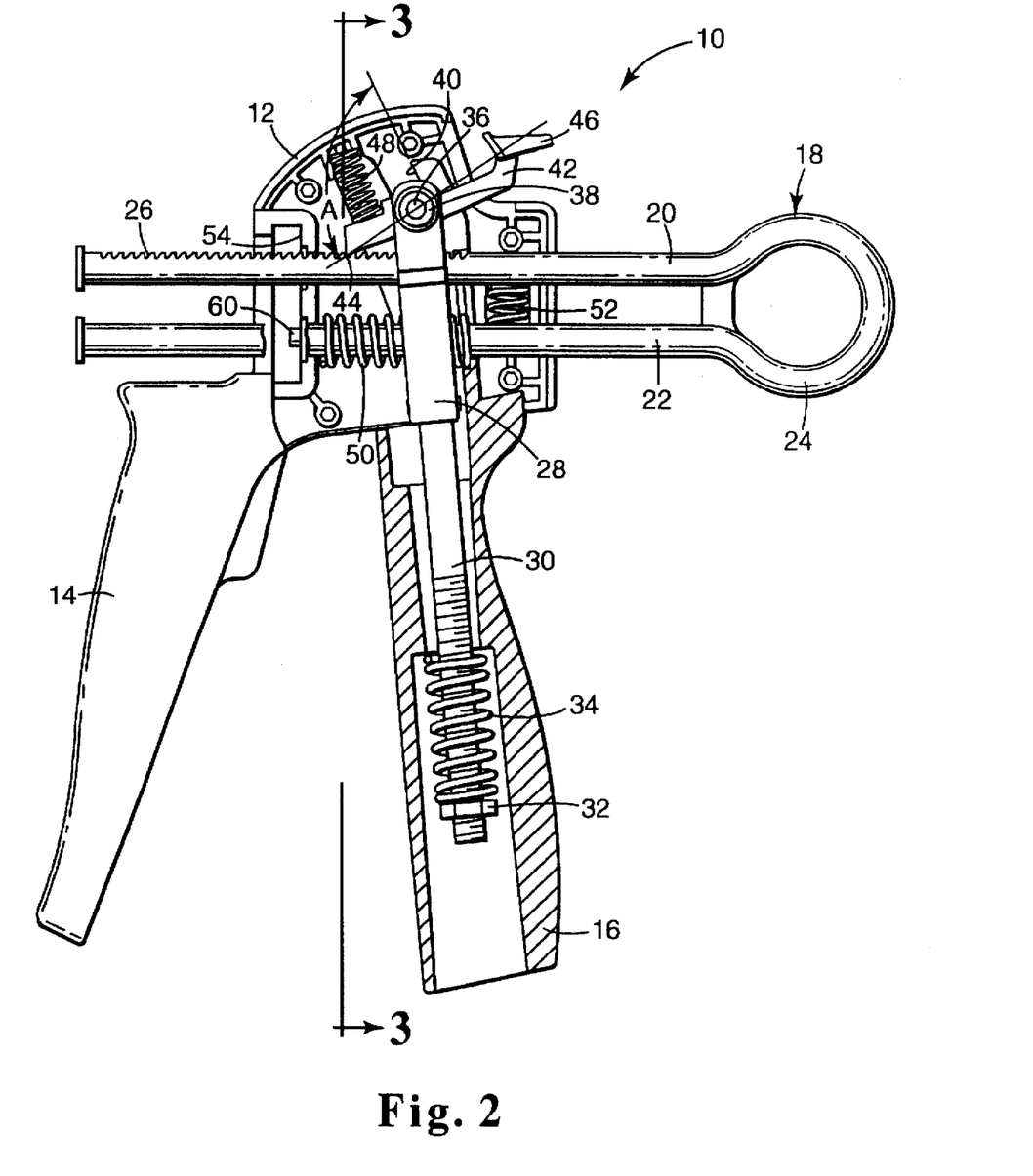
FIG. 2 is a side elevational view in partial section of the applicator shown in FIG. 1, wherein the container and static mixing assembly have been removed.
Figure 4:
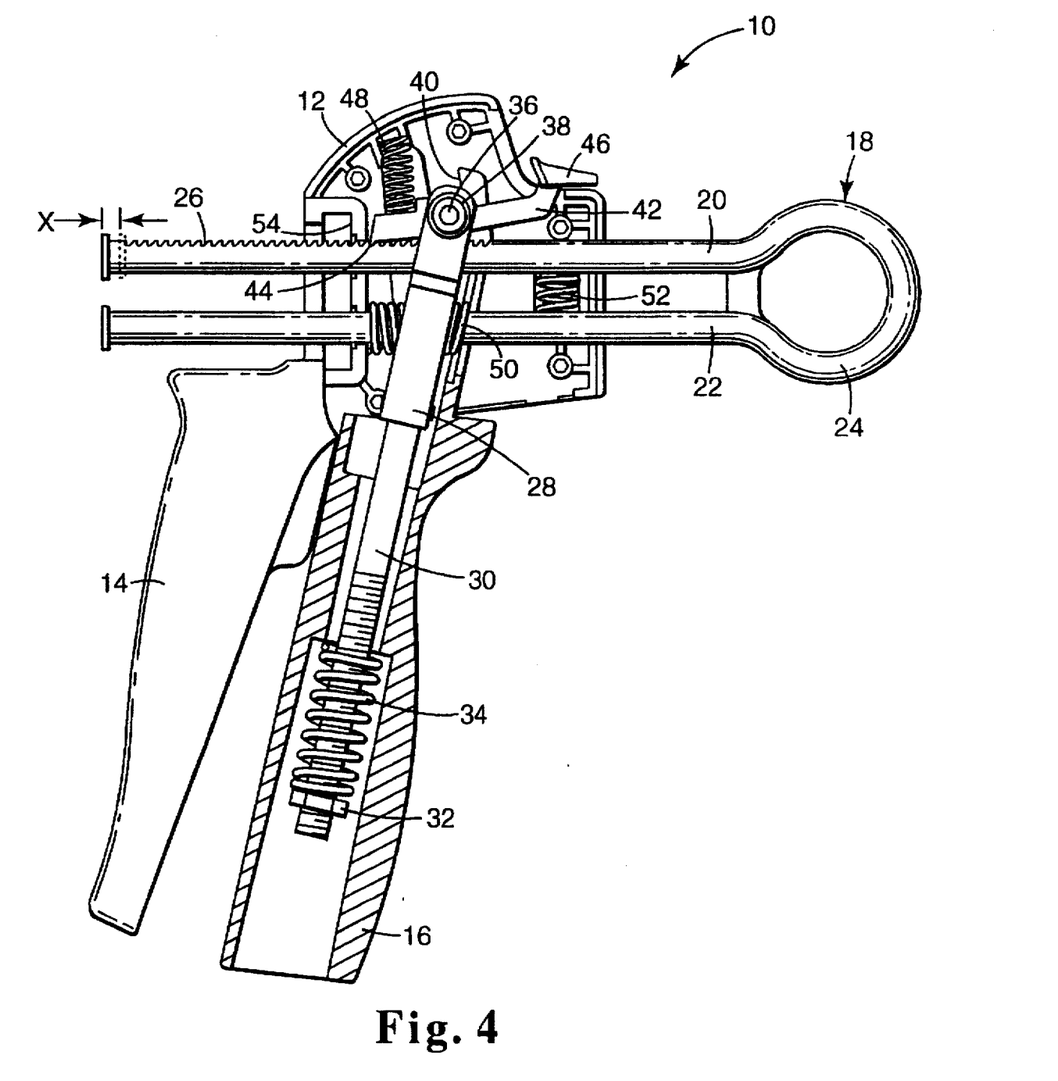
FIG. 4 is a view somewhat similar to FIG. 2 except that a handle of the applicator has been moved about a pair of pivot bosses, causing a follower to advance a plunger of the applicator.
Figure 5:
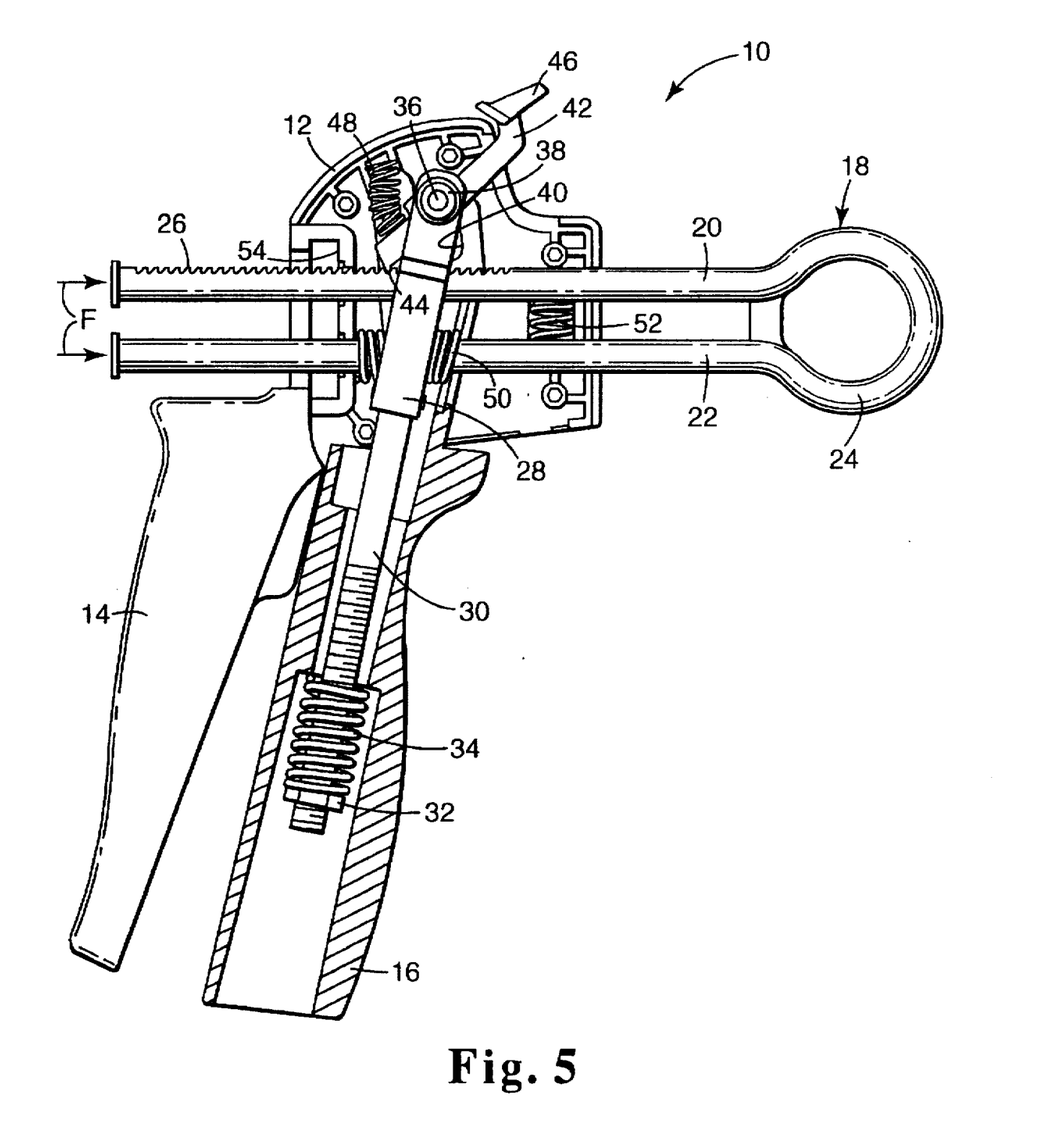
FIG. 5 is a view somewhat similar to FIG. 4 except that the clutch is shown as activated in order to preclude further advancement of the plunger, as may occur whenever movement of the plunger is hindered by resistance that is greater than a certain value.

A yoke 28 of a clutch of the applicator 10 extends along both sides of the plunger 18 within the hollow portion of the housing 12 and within the upper bifurcated portion of the arm 16. A lower crossbar of the yoke 28 has a hole that receives a shaft of a bolt 30. As illustrated in FIG. 2, the bolt 30 includes a head that rests against the crossbar of the yoke 28, and the lower threaded portion of the bolt 30 receives a nut 32. A coiled compression clutch spring 34 surrounds the bolt 30 and bears against the nut 32 as well as a shoulder formed in the hollow recess of the arm 16. As shown in FIGS. 2, 4 and 5, the spring 34 extends at a non-zero angle relative to the forward, longitudinal direction of movement of the plunger 18.

A pivot pin 36 extends through aligned holes of the upper, spaced apart ends of the yoke 28, and each end of the pivot pin 36 extends through a bushing 38. Each of the two bushings 38 is received in a slot 40 of a respective one of the upper bifurcated end portions of the arm 16.

A ratchet mechanism of the applicator 10 includes a first pawl or follower 42. A central portion of the pin 36 extends through a hole of the follower 42. The follower 42 includes a chisel-shaped lower front edge 44 for engagement with the upper plunger rod 20 in the spaces between adjacent rack teeth 26. A rear, upper portion of the follower 42 extends through an opening in the housing 12 and terminates as a tab 46.

A coiled compression ratchet spring 48 urges the front edge 44 of the follower 42 into releasable engagement with the rack teeth 26. The ratchet spring 48 extends between an upstanding boss that is located on a top surface of a front portion of the follower 42 and a depending socket that is molded on the upper inside wall of the housing 12, both of which serve to retain the ratchet spring 48 in place. The ratchet spring 48 urges the follower 42 in a counter-clockwise direction (viewing, for example, FIG. 2) in an arc about the pivot pin 36. As an alternative, the spring 48 could be replaced by a coil spring having a torsion spring configuration; in such an instance, the coil could be received around a pivot pin extending through the arm 16 and into the housing 12, or alternatively around a post (such as one of the assembly posts used to connect the two sections of the housing together).

A coiled compression return spring 50 is located in the hollow portion of the housing 12 and is received around a portion of the lower plunger rod 22. A front end of the return spring 50 bears against the inner wall of the housing 12, while a rear end of the return spring 50 bears against an upper, rear portion of the arm 16. The return spring 50 urges the arm 16 in a counter-clockwise direction (viewing, for example, FIGS. 1–2) in a rearwardly direction away from the handle 14 and in an arc about the pivot bosses 75 (FIG. 3).

A coiled compression drag spring 52 is also located within the hollow upper portion of the housing 12 and bears against adjacent sides of the plunger rods 20, 22. The drag spring 52 is retained in place by inner projections formed in the housing 12. The drag spring 52 functions to hinder rearward movement of the plunger 18 when the arm 16 is released for movement of the front edge 44 in a rearward direction along the row of teeth 26, as may occur when it is desired to advance the ratchet mechanism for subsequent additional forward movement of the plunger 18. Preferably, the springs 34, 48, 50, 52, the follower 44, the arm 16, the plunger 18 and other components of the applicator 10 other than the housing 12 are made of a metallic material (such as stainless steel) that is suitable for repeated autoclaving or chemical sterilization.

Figure 1:
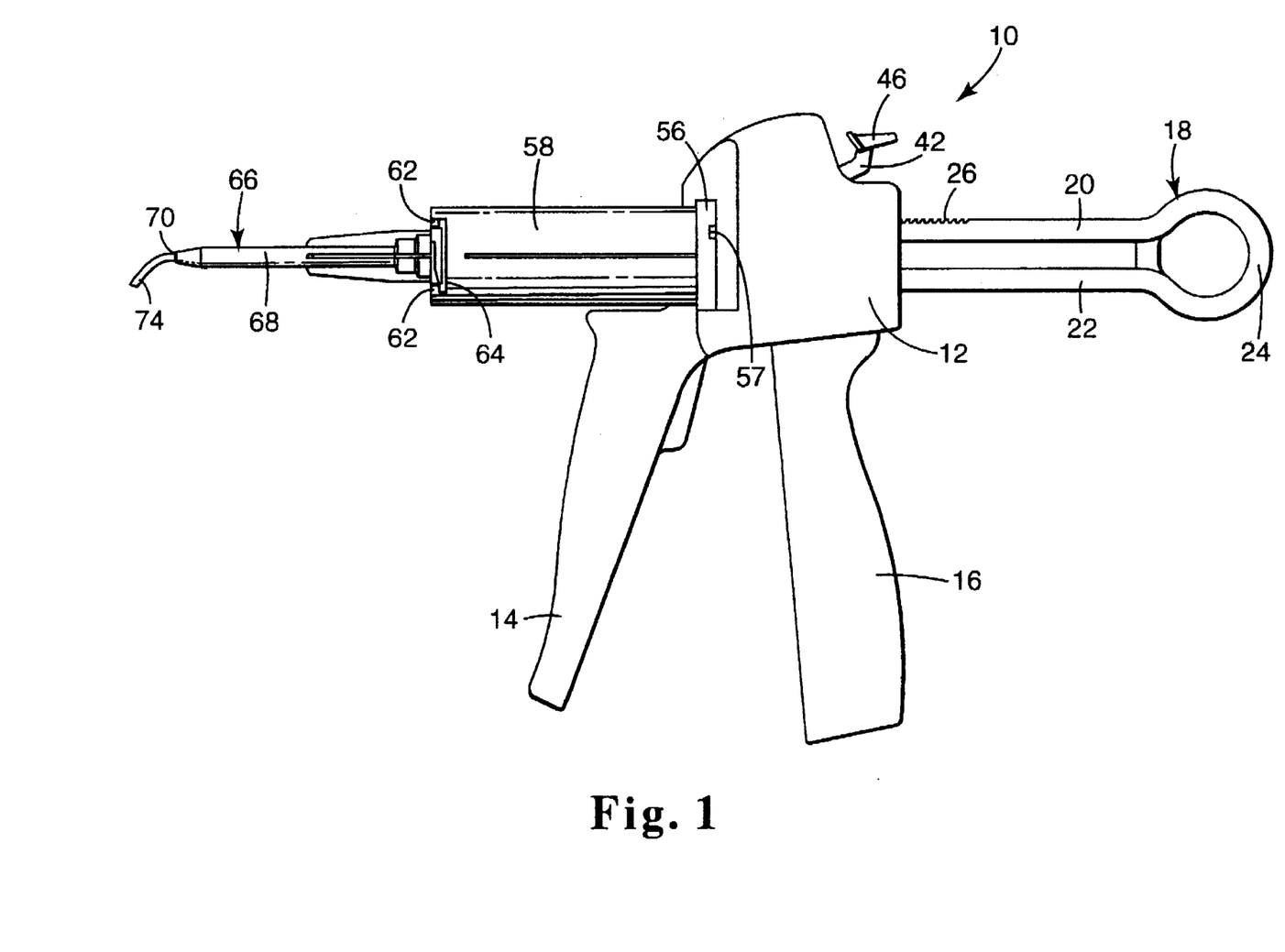
FIG. 1 is a side elevational view of an applicator having a clutch constructed in accordance with the principles of the present invention, and also showing a dispensing container and static mixing assembly coupled to the applicator.

The applicator housing 12 includes a generally C-shaped receptacle 54 that complementally receives a flange 56 (see FIG. 1) of a double-barrel cartridge or container 58. The flange 56 includes two recesses 57 (one of which is shown in FIG. 1) located on opposite sides of the flange 56. The container 58 includes an upper cylindrical chamber and a lower cylindrical chamber that lie in parallel, side-by-side relation to each other, and a piston (not shown) is received in each chamber. Each chamber contains a different component of the material to be mixed and dispensed.

The housing 12 includes a tab 60 that is shown in FIG. 2. The tab 60 is located in the receptacle 54 and is behind the lower plunger rod 22 in FIGS. 4 and 5. The tab 60 is matingly received in one of the two recesses 57 of the flange 56 as the flange 56 is received in the receptacle 54. The tab and recess are useful to insure that the applicator 10 is used only with certain cartridges such as the container 58. Examples of alternative constructions of the recess and tab are described in abandoned U.S. patent application Ser. No. 08/394,724, entitled "Dual Chamber Cartridge Dispensing System for Dental Material", filed on Feb. 27, 1995 and assigned to the assignee of the present invention, the disclosure of which is expressly incorporated by reference herein.

The container 58 is preferably integrally molded of an amorphous polyolefin such as is sold under the trade name "ZEONEX" grade 480 (from Nippon Zeon Co., Ltd., Tokyo, Japan). Alternatively, the container can be made of a polyethylene such as is sold under the trade name "ALATHON H5618" (from Occidental Chemical Corporation, Dallas, Tex.) or a polypropylene resin such as is sold under the trade name "FINA 3467" (from Fina Oil and Chemical Company, Deer Park, Tex.). Further information regarding the container material is set out in U.S. Pat. No. 5,624,260 entitled "DELIVERY SYSTEM FOR AQUEOUS PASTE DENTAL MATERIALS", the disclosure of which is expressly incorporated by reference herein.

The front end of the container 58 includes two "L" shaped ears 62 that are adapted to releasably engage a plate 64 of a static mixing assembly 66 and form a bayonet-style coupling. Before the static mixing assembly 66 is coupled to the container 58, the ears 62 may be used to releasably engage a shipping cap. A suitable shipping cap and an optional induction seal for covering front openings of the container 58 are described in U.S. Pat. No. 5,236,108 that is assigned to the assignee of the present invention and that is expressly incorporated by reference herein.

The static mixing assembly 66 includes an exit conduit 68 that is integrally connected to the plate 64. The exit conduit 68 includes a rear cylindrical chamber that fits over a neck of the container 58 when the plate 64 is connected to the ears 62. The exit conduit 68 also includes a second, somewhat smaller cylindrical chamber in front of the chamber surrounding the neck, and an internal cylindrical cavity of the exit conduit 68 extends forwardly from the second inner chamber toward a front opening 70.

The plate 64 has a somewhat oval-shaped configuration, and the thickness of the portion of the plate 64 that fits behind the ears 62 varies. As the plate 64 is placed over the neck of the container 58 and as the exit conduit 68 is turned about its longitudinal axis, the plate 64 releasably locks into tight engagement with the container 58 between the ears 62 and a front end of the container 58. The exit conduit 68 also includes four spaced-apart, longitudinally extending strengthening ribs that integrally connect the plate 64 and a middle portion of the exit conduit 68.

A static mixing element (not shown) is received in a cavity of the exit conduit 68. The static mixing element includes an integrally joined series of helical, auger-like or "bow-tie" mixing segments that successively subdivide, rotate and recombine the incoming component streams from the container 58. The static mixing element is held in place in the cavity by frictional engagement with the inner walls of the cavity. The static mixing element may be made of polypropylene (such as "PROFAX" brand, no. 6331NW; from Himont USA, Wilmington, Del.) and have an appearance similar to that shown in U.S. Pat. No. 4,538,920. A suitable material for the exit conduit 68 is nylon (such as "ZYTEL" brand, no. 101L; from DuPont) that is tinted to an orange color to block passage of actinic radiation.

An elongated, metal cannula 74 extends through and outwardly away from the front opening 70. The cannula 74 has an outwardly flared rear section that is located in the cavity of the exit conduit 68 between the front of the static mixing element and the opening 70. The flared rear section of the cannula 74 engages an inner, conical wall section of the cavity of the exit conduit 68, where the exit conduit 68 is necked down in tapered fashion.

A cannula 74 is elongated and curved in a direction along its longitudinal axis as illustrated in FIG. 1. Other configurations are also possible, including straight or angled configurations. Preferably, the cannula 74 is bendable as needed by finger pressure. The cannula 74 is swivelable about its longitudinal axis relative to the exit conduit 68.

Operation of the invention will now be described in connection with the embodiment shown in FIGS. 1–5. To advance the plunger 18 and dispense material, the applicator 10 is grasped by the handle 14, and the arm 16 is pivoted approximately 20° in an arc about the bosses 75 from the initial, rest orientation as is illustrated in FIG. 2 and to a forward orientation as is shown in FIG. 4. The front edge 44 of the follower 42 drivingly engages the teeth 26 during movement of the arm 16 toward the handle 14 in order to advance the plunger 18. The angle designated "A" in FIG. 2 represents the angle between a first reference plane extending between the pivot pin 36 and the front follower edge 44 and a second reference plane parallel with edges of the arm 16 that define the slot 40. The angle A is greater than 90°.

As the arm 16 is moved to its forward orientation as depicted in FIG. 4, the follower 42 moves the plunger 18 forward a distance designated "X". The moving plunger 18 advances the pistons in the container 58, such that material in each chamber of the container 58 is directed to the static mixing assembly 66 and ultimately through the cannula 74.

Upon release of the arm 16, the return spring 50 urges the arm 16 in a rearward direction away from the handle 14 and back to its initial rest orientation as shown in FIG. 2. Frictional engagement of the drag spring 52 with the plunger rods 20, 22 tends to restrict rearward movement of the plunger 18 to a degree sufficient to enable the front edge 44 of the follower 42 to slightly swing in a clockwise direction viewing FIGS. 2 and 4–5, so that the front edge 44 rides over the top of the teeth 26 as the arm 16 moves rearwardly.

When it is desired to move the plunger 18 in a rearwardly direction, the user may depress the tab 46 in order to pivot the follower 42 in a clockwise direction and disengage the front edge 44 from the teeth 26. When the tab 46 is depressed in this manner, the user can grasp the ring 24 to pull the plunger 18 in a rearwardly direction.

FIG. 5 shows an illustration for exemplary purposes of the clutch of the applicator 10 in its fully activated position when the arm 16 is pivoted in an arc approximately 20° about the bosses 75. The force designated "F" in FIG. 5 represents a resistive force that is preferably less than a force that would burst the container 58 or break, strain or otherwise damage components of the applicator 10. Preferably, the sum of the forces "F" sufficient to activate the clutch is any force that is in the range of 45–60 kg.

When the plunger 18 encounters the forces "F", the follower 42 pivots in a counter-clockwise direction (when viewing FIG. 5) about the front edge 44 of the follower 42. The sum of the forces "F" is sufficient to overcome the friction between the bushings 38 and the slots 40 and the bias presented by the clutch spring 34 and enable the pivot pin 36 (along with the yoke 28) to rise in the slot 40 as the arm 16 continues to pivot toward its forward orientation. The sum of the forces "F" is also sufficient to overcome the relatively small bias presented by the follower spring 48. As the yoke 28 rises within the hollow portion of the housing 12, the bolt 30 moves upwardly within the hollow recess of the arm 16 and compresses the clutch spring 34 as shown in FIG. 5.

Consequently, the clutch of the applicator 10 enables energy as provided by the user to move the arm 16 to be transferred to the pivotal motion of the follower 42 about the front edge 44, as well as to the upward movement of the bolt 30 against the biasing force of the clutch spring 34 whenever the sum of the resistive forces "F" is greater than a certain value such as 45 kg. In such an instance, energy supplied by the arm 16 is no longer used to advance the plunger 18. Advantageously, the clutch operates in a smooth manner during activation, without a snap or toggle feeling as may be imparted by other clutch constructions.

The upward movement of the follower 42 during activation of the clutch enables the tab 46 to rise and thereby provide a visual indication to the user that the force supplied to the arm 16 is excessive and greater than a certain design value. Optionally, an upstanding projection can be connected to the follower 42 in a location between the tab 46 and the pivot pin 36, and the projection could pass through a hole in the top of the housing 12 and be painted with a red color or provided with other identifying means to provide a greater visual indication that the clutch has been activated. Upon release of the arm 16, the clutch spring 34, the return spring 50 and the follower spring 48 enable the arm 16 and the follower 42 to return to their initial, rest positions as illustrated in FIG. 2.

As an alternative, the follower spring 48 and the clutch spring 34 may be replaced by a single spring that is located in the area where the follower spring 48 is shown in the drawings. Such construction would also enable the bolt 30 and the yoke 28 to be eliminated. However, such a combination follower and clutch spring may need to be significantly larger in many instances than the follower spring 48 shown in the drawings such that the top of the housing 12 would need enlargement for accommodating the combination follower and clutch spring. By contrast, the embodiment shown in FIGS. 1-5 is advantageous because the top portion of the housing 12 is relatively small and does not unduly obstruct the view toward the site where the material is to be dispensed. The recess in the arm 16 has sufficient space to easily receive the clutch spring 34.

The tension on the clutch spring 34 may be adjusted by rotation of the nut 32. The nut 32 functions as an adjustment mechanism and, as a result, the total amount of the resistive forces "F" needed to activate the clutch can be varied as needed. Preferably, the nut 32 is adjusted in the factory to a desired specification, and subsequently is either covered or provided with a non-standard outer configuration to discourage adjustment by a casual user.

Another embodiment of the invention is illustrated in FIGS. 6-10 and concerns an applicator 10a for dispensing material from a container. The applicator 10a is substantially identical to the applicator 10 described in connection with the embodiment shown in FIGS. 1-5 with the exception of the elements set out below. More particularly, the applicator 10a includes a housing 12a with a depending handle 14a, an arm return spring (not shown), and a clutch that are essentially the same as the housing 12, handle 14, spring 50 and the clutch respectively that are described above, and as such a detailed description need not be repeated.

Figure 6:
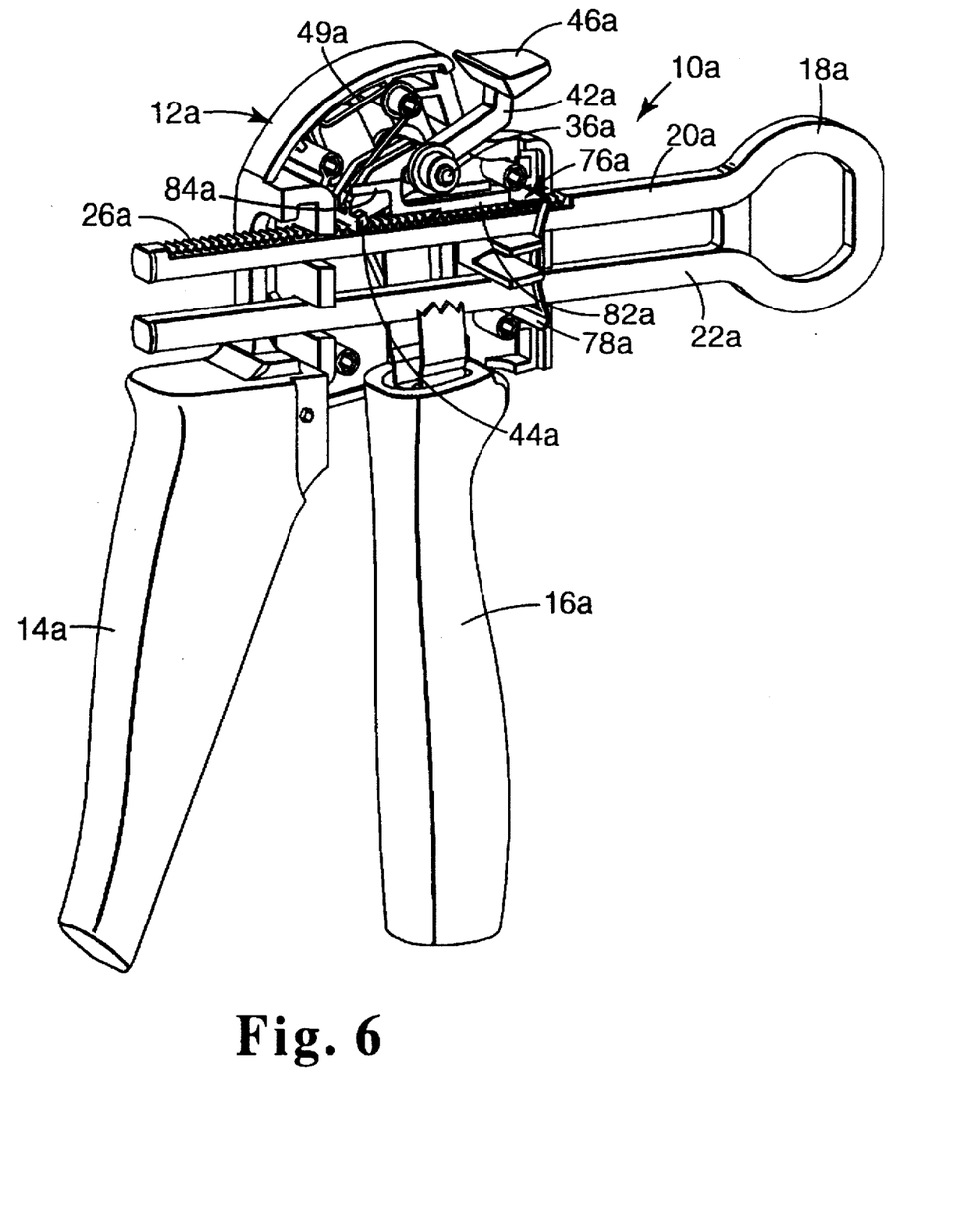
FIG. 6 is a perspective, fragmentary view of an applicator with parts broken away in section in accordance with another embodiment of the present invention, illustrating an integral pawl for hindering rearward movement of the plunger.
Figure 7:
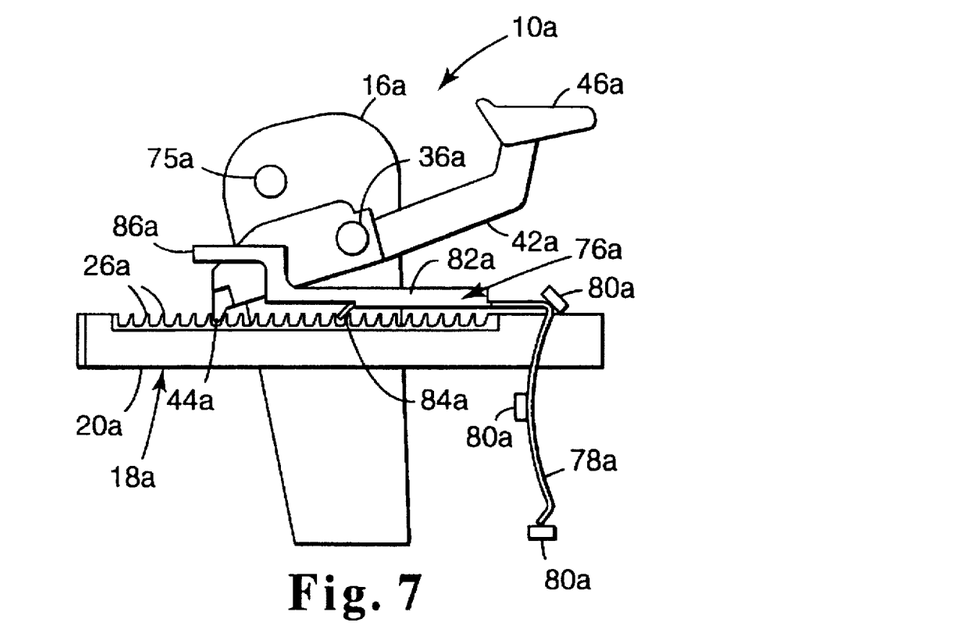
FIG. 7 is a schematic side elevational view of part of the applicator shown in FIG. 6.
Figure 8:
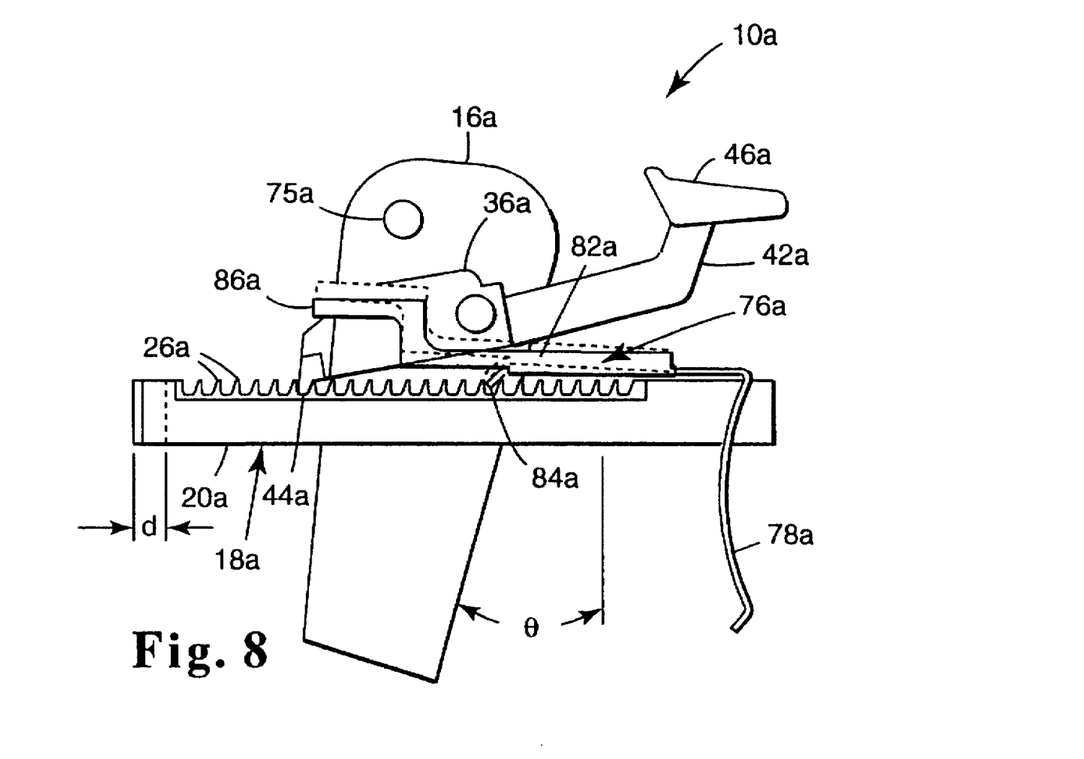
FIG. 8 is a view somewhat similar to FIG. 7 except that an arm of the applicator has been moved to advance the plunger.
Figure 9:
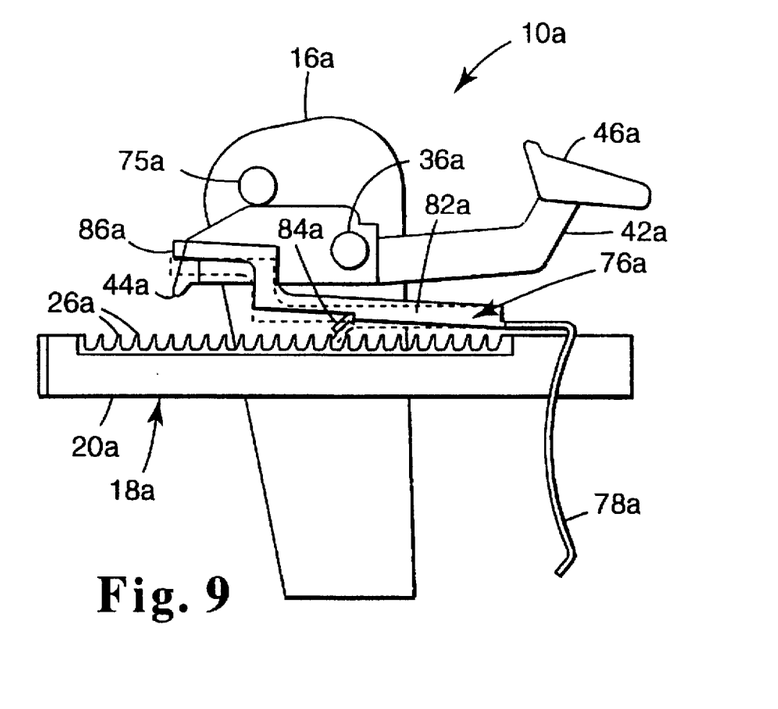
FIG. 9 is a view somewhat similar to FIG. 8 except that the pawl has been lifted from a row of rack teeth on the plunger in order to permit the user to retract the plunger.

An upper portion of an arm 16a of the applicator 10a bifurcated and in the drawings is shown only on one side. The arm 16a is shown for exemplary purposes in FIGS. 7-9 with a somewhat different configuration than its configuration as depicted in FIGS. 1-5, 6 and 10. However, it should be understood in this regard that the operation and function of the arms are essentially the same. In FIGS. 7-9, the arm 16a pivots relative to the housing about a pivot point 75a, which if desired may be embodied by a pair of outwardly extending bosses similar to the bosses 75 illustrated in FIG. 3.

A ratchet mechanism of the applicator 10a includes a follower 42a that is pivotally connected to the arm 16a by a pin 36a. A rear, upper structure or portion of the follower 42a extends through an opening in the housing and terminates as a tab 46a. A front portion of the follower 42a includes a chisel-shaped lower front edge 44a for engagement with an upper plunger rod 20a of a plunger 18a (see FIG. 6) in the spaces between adjacent teeth of a row of rack teeth 26a. The plunger 18a is essentially identical to the plunger 18 described above. As illustrated in FIG. 6, a torsion spring 49a urges the front edge 44a of the follower 42a into releasable engagement with the rack teeth 26a. A lower portion of the torsion spring 49a bears against the bottom of a groove located on the top of the follower 42a, and an upper portion of the spring 49a bears against an inner surface of a top section of the housing 12a.

Figure 10:
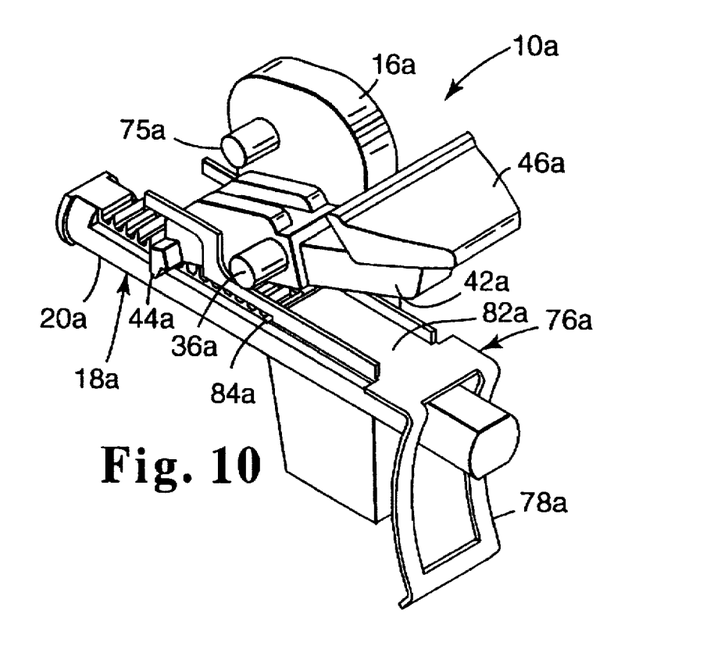
FIG. 10 is a perspective, fragmentary, schematic view of part of the applicator shown in FIG. 6.

A pawl 76a is provided to hinder movement of the plunger in a rearward direction. The pawl 76a has a curved first section 78a that bears against a rear wall of the housing 12a next to holes in the housing 12a for passage of the rods of the plunger 18a. As illustrated in FIGS. 6 and 10, the first section 78a has a rectangular opening that receives the upper plunger rod 20a as well as a lower plunger rod 22a (FIG. 6 only). In FIG. 7, the locations where the first sections 78a bears against the housing 12a are designated by the rectangles numbered 80a.

The pawl 76a includes a second section 82a that is integrally connected to the first section 78a. The second section 82a includes a downwardly inclined portion or tooth 84a that is engagable with the row of rack teeth 26a. Opposite side portions of the second section 82a are bent upwardly in parallel relation.

The pawl 76a also includes a third section 86a that extends outwardly from the second section 82a. The third section 86a includes two segments that extend forwardly from the upstanding, parallel side portions of the second section 82a. An outer or forward end of the third section 86a is offset and extends directly above the front edge 44a. The front edge 44a extends in a transverse direction parallel to the grooves between adjacent rack teeth 26a, and is longer than the distance between the two spaced apart segments of the overlying third section 86a.

The first section 78a, the second section 82a and the third section 86a are integral and made of a resilient material such as spring steel. Suitable materials include half hard type 301 stainless steel. The pawl 76a has a configuration such that the tooth 84a is yieldably biased toward the rack teeth 26a.

In use, the applicator 10a is grasped and the arm 16a is moved in a clockwise direction viewing FIG. 7. As a result, the front edge 44a bears against the rack teeth 26a and advances the plunger 18a in a forwardly direction. As the arm 16a moves from the orientation shown in FIG. 7 to the orientation shown in FIG. 8, the second and third section 82a, 86a of the pawl 76a deflect and move upwardly a slight distance as indicated by the dashed lines in FIG. 8 such that the tooth 84a rides over the underlying rack teeth 26a. Movement of the arm 16a from the orientation shown in FIG. 7 to the orientation shown in FIG. 8 through the arc designated "θ" in FIG. 8 advances the plunger 18a including the upper plunger rod 20a a distance that is represented by the letter "d".

When it is desired to retract the plunger 18a by pulling on the plunger 18a in a rearwardly direction, the user depresses the tab 46a. Depression of the tab 46a pivots the follower 42a about the pin 36a in a clockwise direction viewing FIG. 9. As the follower 42a is pivoted in such a fashion, an upper wall of the front edge 44a engages the bottom of the outer front end of the third section 86a and raises the third section 86a along with the second section 82a from the dashed line orientation and to the full line orientation that is depicted in FIG. 9.

When the second section 82a is raised as shown in FIG. 9, the tooth 84a is lifted out of engagement with the rack teeth 26a. As a consequence, rearward movement of the plunger 18a is now possible. Once the tab 46a is released, the torsion spring 49 a returns the follower 42a to its orientation shown in FIG. 7, and the inherent resiliency of the pawl 76a causes the second section 82a and the third section 86a to return to their respective positions shown in FIG. 7 such that the tooth 84a re-engages the rack teeth 26a.

The integral pawl 76a is an advantage in that it provides a compact construction that is especially useful for smaller applicators such as dental dispensers. Moreover, the pawl 76a is advantageous over the drag spring 52 shown in FIGS.

2 and 4–5, since the drag spring 52 applies friction to the plunger 18 when the plunger 18 is moving in the forward direction as well as in the rearward direction. Such friction not only increases the effort required to advance or retract the plunger 18, but also provides a certain amount of wear over a period of time.

While the foregoing paragraphs have set out a detailed description of the currently preferred embodiments, those skilled in the art can recognize that other modifications, additions and variations are possible without departing from the spirit of the invention. For example, while the drawings illustrate an applicator having a tooth and follower ratchet advancement mechanism, other types of advancement mechanisms (such as those used in many inexpensive, conventional caulking guns) may also be employed. As such, the scope of the invention should not be deemed limited by the preceding detailed description, but only by a fair reading of the claims that follow and their equivalents.

We claim:

1. An applicator for dispensing material from a container comprising:
   a housing having a receptacle for receiving the container of material to be dispensed;
   an elongated plunger coupled to said housing and movable relative to said housing in a forward, longitudinal direction toward said receptacle;
   a handle connected to said housing;
   an arm coupled to said housing adjacent said handle and movable relative to said housing;
   a follower coupled to said arm and having a portion engagable with said plunger for driving movement of said plunger in said forward direction toward said receptacle as said arm is moved relative to said housing; and
   a clutch for substantially preventing movement of said plunger toward said receptacle while said arm is moved relative to said housing whenever movement of said plunger is hindered by resistance that is greater than a certain value, said clutch including a spring that extends at a non-zero angle relative to said forward, longitudinal direction of movement of said plunger, said clutch coupled to a pivot that couples said followers to said arm.

2. An applicator for dispensing material from a container comprising:
   a housing having a receptacle for receiving the container of material to be dispensed;
   an elongated plunger coupled to said housing and movable relative to said housing in a forward, longitudinal direction toward said receptacle;
   a handle connected to said housing;
   an arm coupled to said housing adjacent said handle and movable relative to said housing;
   a follower coupled to said arm and having a portion engagable with said plunger for driving movement of said plunger in said forward direction toward said receptacle as said arm is moved relative to said housing; and
   a clutch for substantially preventing movement of said plunger toward said receptacle while said arm is moved relative to said housing whenever movement of said plunger is hindered by resistance that is greater than a certain value, said clutch including a spring that extends at a non-zero angle relative to said forward, longitudinal direction of movement of said plunger, wherein said follower is pivotally coupled to said arm at a certain location relative to said arm, and wherein said clutch includes structure enabling said certain location to move relative to said arm whenever movement of said plunger is hindered by resistance that is greater than said certain value.

3. The applicator of claim 2, wherein said follower is pivotally coupled to said arm by a pin, and wherein said structure includes at least one slot in said arm that receives said pin.

4. The applicator of claim 3, wherein said clutch includes means biasing said pin toward said certain location.

5. The applicator of claim 4, wherein said means comprises a spring.

6. The applicator of claim 5, wherein said spring provides a certain biasing force on said pin, and said means includes an adjustment mechanism for varying said certain biasing force.

7. The applicator of claim 5, wherein said arm includes a recess, and wherein said spring extends along said recess.

8. The applicator of claim 2, wherein said housing includes an opening, and wherein said follower includes a portion extending through said opening to provide visual indication of movement of said certain location.

9. An applicator for dispensing material from a container comprising:
   a housing having a receptacle for receiving the container of material to be dispensed;
   an elongated plunger coupled to said housing and movable relative to said housing in a forward, longitudinal direction toward said receptacle, said plunger having a row of rack teeth;
   a handle connected to said housing;
   an arm coupled to said housing adjacent said handle and movable relative to said housing;
   a follower coupled to said arm and having a portion engagable with said row of rack teeth for driving movement of said plunger in said forward direction toward said receptacle as said arm is moved relative to said housing;
   a pawl for hindering movement of said plunger in a rearward direction away from said receptacle, said pawl having a first section connected to said housing and a second section having a tooth engagable with said row of rack teeth, said first section and said second section being integral and made of a resilient material such that said tooth is yieldably biased toward said row of rack teeth; and
   structure extending through said housing for bending said second section relative to said first section in order to disengage said tooth from said plunger when desired.

10. The applicator of claim 9, wherein said first section and said second section together present a generally "L"-shaped configuration.

11. The applicator of claim 9 and including a clutch for substantially preventing movement of said plunger toward said receptacle while said arm is moved relative to said housing whenever movement of said plunger is hindered by resistance that is greater than a certain value.

12. The applicator of claim 9, wherein said structure is integrally connected to said pawl.

13. An applicator for dispensing material from a container comprising:
   a housing having a receptacle for receiving the container of mate rial to be dispensed;
   an elongated plunger coupled t o said housing and movable relative to said housing in a forward longitudinal direction toward said receptacle, said plunger having a row of rack teeth;

a handle connected to said housing;

an arm coupled to said housing adjacent said handle and movable relative to said housing;

a follower coupled to said arm and having a portion engagable with said row of rack teeth for driving movement of said plunger in said forward direction toward said receptacle as said arm is moved relative to said housing; and a pawl for hindering movement of said plunger in a rearward direction away from said receptacle, said pawl having a first section connected to said housing and a second section having a tooth engagable with said row of rack teeth, said first section and said second section being integral and made of a resilient material such that said tooth is yieldably biased toward said row of rack teeth, wherein said first section has an opening and wherein said plunger extends through said opening.

14. An applicator for dispensing material from a container comprising:

a housing having a receptacle for receiving the container of material to be dispensed;

an elongated plunger coupled to said housing and movable relative to said housing in a forward longitudinal direction toward said receptacle, said plunger having a row of rack teeth;

a handle connected to said housing;

an arm coupled to said housing adjacent said handle and movable relative to said housing;

a follower coupled to said arm and having a portion engagable with said row of rack teeth for driving movement of said plunger in said forward direction toward said receptacle as said arm is moved relative to said housing; and a pawl for hindering movement of said plunger in a rearward direction away from said receptacle, said pawl having a first section connected to said housing and a second section having a tooth engagable with said row of rack teeth, said first section and said second section being integral and made of a resilient material such that said tooth is yieldably biased toward said row of rack teeth, wherein said pawl includes a third section extending outwardly from said second section for moving said second section relative to said plunger when desired in order to disengage said tooth from said row of rack teeth, wherein said third section comprises a pair of spaced apart segments, and wherein said follower extends between said segments.

15. An applicator for dispensing material from a container comprising:

a housing having a receptacle for receiving the container of material to be dispensed;

an elongated plunger coupled to said housing and movable relative to said housing in a forward, longitudinal direction toward said receptacle, said plunger having a row of rack teeth;

a handle connected to said housing;

an arm coupled to said housing adjacent said handle and movable relative to said housing;

a follower coupled to said arm and having a portion engagable with said row of rack teeth for driving movement of said plunger in said forward direction toward said receptacle as said arm is moved relative to said housing; and a pawl for hindering movement of said plunger in a rearward direction away from said receptacle, said pawl having a first section connected to said housing and a second section having a tooth engagable with said row of rack teeth, said first section and said second section being integral and made of a resilient material such that said tooth is yieldably biased toward said row of rack teeth, wherein said pawl includes a third section extending outwardly from said second section for moving said second section relative to said plunger when desired in order to disengage said tooth from said row of rack teeth, wherein said follower includes a portion extending through said housing, and wherein said follower is engagable with said third section of said pawl for moving said second section relative to said plunger when desired.

16. The applicator of claim 15, wherein said follower is pivotally coupled to said arm.

17. An applicator for dispensing material from a container comprising:

a housing having a receptacle for receiving the container of material to be dispensed;

an elongated plunger coupled to said housing and movable relative to said housing in a forward, longitudinal direction toward said receptacle, said plunger having a row of rack teeth;

a handle connected to said housing;

an arm coupled to said housing adjacent said handle and movable relative to said housing;

a follower coupled to said arm and having a portion engagable with said row of rack teeth for driving movement of said plunger in said forward direction toward said receptacle as said arm is moved relative to said housing;

a pawl for hindering movement of said plunger in a rearward direction away from said receptacle, said pawl having a first section connected to said housing and a second section having a tooth engagable with said row of rack teeth, said first section and said second section being integral and made of a resilient material such that said tooth is yieldably biased toward said row of rack teeth; and a clutch for substantially preventing movement of said plunger toward said receptacle while said arm is moved relative to said housing whenever movement of said plunger is hindered by resistance that is greater than a certain value, wherein said follower is pivotally coupled to said arm at a certain location relative to said arm, and wherein said clutch includes structure enabling said certain location to move relative to said arm whenever movement of said plunger is hindered by resistance that is greater than said certain value.

* * * * *